United States Patent [19]
Dussault et al.

[11] Patent Number: 5,493,890
[45] Date of Patent: Feb. 27, 1996

[54] APPARATUS AND METHOD FOR CALIBRATING VAPOR/PARTICLE DETECTION DEVICES

[75] Inventors: Daniel A. Dussault, Newburyport; William A. Curby, Boston, both of Mass.; Stephen J. MacDonald, Salem, N.H.; Edward E. A. Bromberg, Peabody, Mass.

[73] Assignee: Thermedics Detection Inc., Chelmsford, Mass.

[21] Appl. No.: 213,988

[22] Filed: Mar. 16, 1994

[51] Int. Cl.⁶ .......................... G01N 33/94; G01N 37/00
[52] U.S. Cl. .......................... 73/1 G; 73/23.41; 73/23.40; 86/1.1
[58] Field of Search .......................... 73/1 G, 23.4, 23.41, 73/167, 863.12, 864.33; 86/1.1, 50

[56] References Cited

U.S. PATENT DOCUMENTS

| | | | |
|---|---|---|---|
| 3,430,482 | 3/1969 | Dravnieks | 73/23.41 |
| 3,925,022 | 12/1975 | Showalter et al. | 73/23.41 |
| 4,164,861 | 8/1979 | Schlereth et al. | 73/1 G |
| 4,896,547 | 1/1990 | Arney et al. | 73/863.81 |
| 4,909,090 | 3/1990 | McGown et al. | 73/863.12 |
| 5,092,155 | 3/1992 | Rounbehler et al. | 73/23.41 |

*Primary Examiner*—Robert Raevis
*Assistant Examiner*—Daniel S. Larkin
*Attorney, Agent, or Firm*—Fish & Richardson

[57] ABSTRACT

A method and apparatus for calibrating contraband vapor/particle detection devices is described. The invention includes a desorb site onto which may be deposited solutions containing known concentrations of one or more of the specific compounds to be detected. The desorb site, which may be rapidly heated to vaporize the particles contained in the solution deposited on its surface, is housed in a sealable chamber. The vapor and/or particles become entrained in an air stream forced across the surface of the desorb site, and the airstream is then delivered through a snout to the contraband vapor particle detector.

17 Claims, 2 Drawing Sheets

# APPARATUS AND METHOD FOR CALIBRATING VAPOR/PARTICLE DETECTION DEVICES

STATEMENT AS TO FEDERALLY SPONSORED RESEARCH

This invention was made with Government support under Contract DTFA03-87-C-00003. The Government has certain rights in this invention.

BACKGROUND OF THE INVENTION

The present invention relates in general to vapor/particle detection devices, and more particularly concerns novel apparatus and methods for quickly, easily, and inexpensively calibrating vapor/particle detection devices. Examples of vapor/particle detection devices are described in U.S. Pat. No. 5,092,217 to Achter et al., entitled "Method of Calibrating a Vapor Detector," issued on Mar. 3, 1992, assigned to the assignee of the present invention, and incorporated herein by reference in its entirety.

Increasing interest in detecting the presence of contraband substances, such as explosives, controlled narcotics, perfumes, interferents, and numerous other materials, has led many organizations worldwide, most notably airports, to purchase vapor/particle detection devices. These detectors, which are able to collect, analyze, and identify trace amounts of substances entrained in an airstream, are generally of either of two types. The first type is a hand-held "gun" detector, a device sufficiently portable to be carried to the object or person to be tested. The second type is a stationary "portal" detector, a chamber or booth within which objects or persons are tested.

For vapor/particle detectors of either type to remain effective, the device must be periodically calibrated and adjusted or otherwise serviced as necessary. Calibration can involve either a general, "front-to-back" qualitative assessment of whether the detector properly indicates the presence of contraband, or a particularized determination of the actual, quantitative sensitivity of the detector.

Frequent calibrations can be of particular importance in many field applications of vapor/particle detectors. In the field, generally only a small fraction of the sampled items contain contraband substances, making positive indications a rare occurrence. Thus, because the continued absence of positive indications is unremarkable, frequent calibration serves two important purposes. First, it determines whether the threshold of detection has drifted unacceptably. Second, it keeps the operator familiar with the general operation of the equipment, and how it responds to the presence of contraband.

The need frequently to calibrate vapor/particle detectors can however be complicated by the fact that the system operator typically has no or only moderate technical training. A cumbersome and difficult calibration procedure is thus more likely to be mishandled or foregone completely. Similarly, if the necessary calibration equipment is not sufficiently portable to be included within, or brought to, the portal, the difficulty and expense of calibration increases.

The calibration of portal detectors poses further difficulties as well. In particular, because the airflow characteristics through a portal are rarely uniform, certain regions of the portal will be more sensitive than others. A calibration technique or apparatus that is unable to isolate and quantify these spatial variations in sensitivity therefore provides a less-complete picture of overall detector performance.

Determining detector sensitivity quickly, easily, and accurately is important also during the design and testing of vapor/particle detection devices. As with field testing, it is of course important to evaluate the qualitative front-to-back performance of the detector periodically under a variety of conditions. Quantitative sensitivity evaluation is also of particular value to the detector designer. Generally, vapor/particle detection devices include a "sample collector train," which collects and concentrates vapor and/or particles entrained in a stream of sample air. Because these collector trains have complex heat transfer and air flow properties, slight changes in their design can lead to dramatic shifts in performance. In the absence of a calibration technique and/or apparatus that allows the sensitivity of the detector to be accurately evaluated, detector designers may be unable to determine the impact of a given design change on collector efficiently and (in the case of portal detectors) spacial sensitivity.

One calibration technique is to employ actual contraband, such as narcotics or explosives, in a setting that reflects real world conditions (e.g., on a person or in luggage). Field operators, however, are generally untrained in the handling of most contraband compounds, making this technique unacceptable for most field testing purposes, particularly the calibration of portal-type explosive detectors located in heavily populated areas. Even when designing and testing detectors in the laboratory, where using individuals highly trained in the handling of contraband is more practical, the frequency at which testing must be performed renders this approach undesirable.

Alternative calibration techniques rely on solutions prepared by dissolving known quantities of a particular contraband in a fixed amount of solvent to yield a solution having a known concentration of contraband. In one of these techniques, the detector is opened and the solution is applied directly to the collector train. This approach, however, may prove difficult and time-consuming for the lay operator. Further, while this technique may be helpful to determine how effectively the detector measures the quantity of substance disposed on the collector, it says little about either how well that substance is collected from the airstream, or whether the airstream is properly funnelled past the collector.

The contraband solution can instead be applied to a sorbent material, such as a paper towel or a gauze pad. When later sampled by a hand-held explosive detector or brought into a portal, these pads emit vapors and/or particles that replicate those discharged by an actual contraband sample. This technique, while relatively easy to perform, is generally only suitable for front-to-back qualitative analysis; that is, determining whether the detector properly indicates the presence of some critical amount of contraband. The concentration of vapors or particles is not known accurately enough to allow for reliable, repeatable quantitative sensitivity analysis.

Summary of the Invention

The invention features an apparatus and method for calibrating a detector of contraband vapors and/or particles that includes a desorb site onto which solutions containing known concentrations of one or more of the specific compounds to be detected may be deposited. The desorb site, which may be rapidly heated to vaporize and/or drive vapors from the residue left after evaporation of the solvent, is housed in a sealable chamber. An air inlet is positioned such that air introduced into the chamber flows across the surface of the desorb site and exits through a snout.

In one exemplary embodiment, the snout is heated, such that vapor exiting the sealable chamber does not condense on the interior snout walls. Preferably also, the desorb site is similar in design to the high-efficiency sample collector trains used in vapor/particle detection devices.

The invention offers a point source of vapor having a known concentration of contraband. Because the total amount of contraband vapor produced by the invention is also known to a high degree of accuracy, the invention allows a field operator or detector designer to determine how efficiently a detector captures and measures vapors from the available airstream. Because the contraband vapor emanates from a single outlet point source, the invention is useful also for determining whether and how the sensitivity of a portal-type detector varies spatially. Thus, the invention is suitable for both qualitative and quantitative calibration.

Furthermore, the invention may be contained in a reasonably small, transportable package that is easily opened for access to the desorb site. It is therefore suitable for use by relatively untrained personnel for calibrating portal and other detectors located in the field.

Other advantages and features of the invention will be apparent from the following description of a preferred embodiment, and from the claims.

DESCRIPTION OF THE PREFERRED EMBODIMENT(S)

Figure 1:
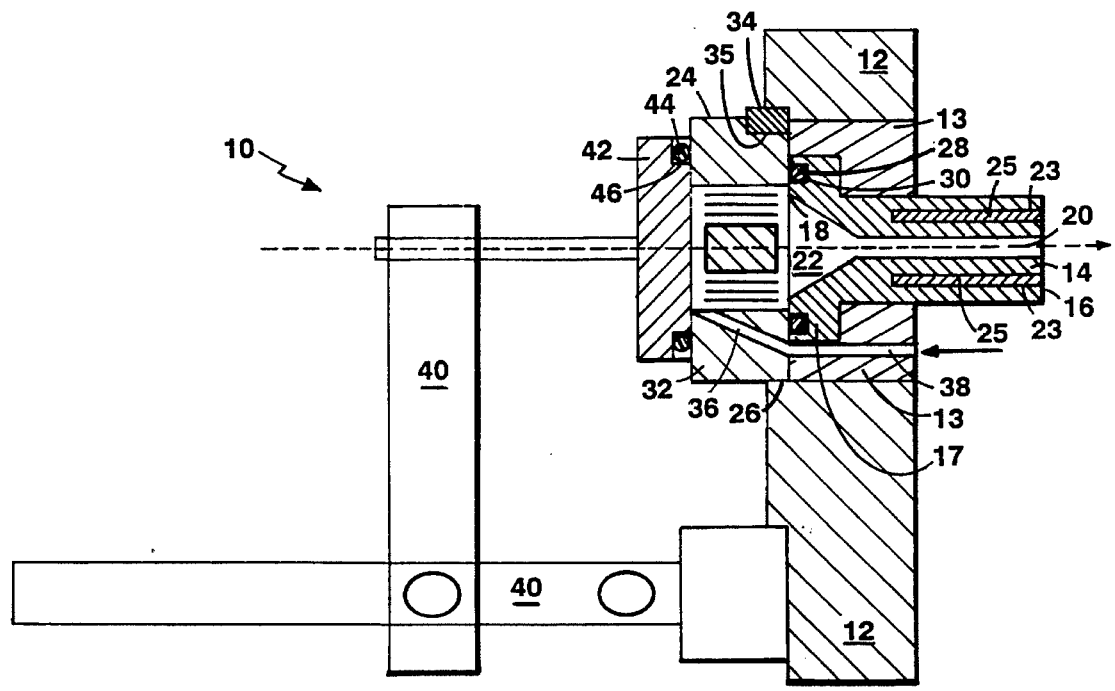
FIG. 1 is a partially broken-away schematic side view diagram of one embodiment of a pulse contraband vapor generator apparatus according to the present invention.
Figure 2:
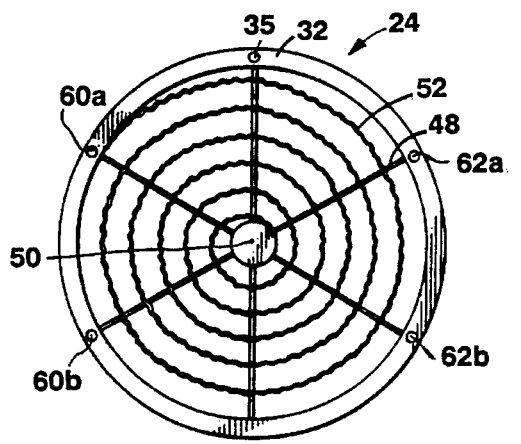
FIG. 2 is an end view of a desorb site subassembly of the apparatus of FIG. 1 utilizing a spiral-wound metal ribbon as a substrate.

A schematic of a pulse contraband vapor generator 10 for use in calibrating a contraband vapor and/or particle detector is shown in FIG. 1. A mounting plate 12 in vapor generator 10 supports an insulating sleeve 13 (made of an electrically and thermally insulating material, such as bakelite), which in turn supports a snout 14. The distal end 16 of snout 14 projects outward from the front surfaces of mounting plate 12 and insulating sleeve 13. A flange 17 at the proximal end 18 of snout 14 lies flush with the back surface of insulating sleeve 13. Snout 14 defines an interior air flow passage 20 extending the length of snout 14. The cross-section of passage 20 is generally uniform, except at the proximal end of the snout 14 where it widens to form a frusto-conical funnel 22.

Snout 14 also includes a pair of heater rod holes 23 that lie parallel to, and on opposite sides of, passage 20. Heater rod holes 23 do not extend into either passage 20 or frusto-conical funnel 22, and are of sufficient dimension to accommodate a pair of heater rods 25. Heater rods 25 are controlled by a thermostatic controller (not shown) that, when energized, regulates the heater rods 25 to heat the entire outer surface of passage 20 to a generally constant and uniform preset temperature.

A collector/desorb subassembly 24 positioned on the proximal surface 18 of snout 14 is oriented radially by a shoulder region 26 of mounting plate 12. Shoulder region 26 ensures that the collector/desorb subassembly 24 remains concentric with passage 20. An O-ring 28 installed into a concentric O-ring gland 30 in the proximal surface 18 of snout 14 engages an outer hub 32 of collector/desorb subassembly 24, providing a sealed interface between outer hub 32 and snout 14. A pin 34 protruding from the back side of mounting plate 12 engages a recess 35 in the circumference of outer hub 32, rotationally positioning collector/desorb subassembly 24. Pin 34 thus ensures that the inlet of an airflow passage 36 in outer hub 32 aligns with the outlet of a hollow tube (made of, e.g., stainless steel) passing through insulating sleeve 13. The inlet of tube 38 connects to a valved source of filtered, pressurized air (not shown). O-rings (not shown) at both the inlet and the outlet of tube 38 ensure that the fluid flow path between the air source and airflow passage 36 remains sealed. The outlet of airflow passage 36 opens into the interior of outer hub 32, and is oriented to cause air exiting the outlet to flow radially inward at the back of collector/desorb subassembly 24.

Connected also to mounting plate 12 is a clamp 40 to which a sealing back plate 42 attaches. When clamp 40 is closed, an O-ring 44 in an O-ring gland 46 on the front surface of the sealing back plate 42 engages the back face of the outer hub 32, sealing the interface between the hub 32 and the back plate 42, and maintaining the axial alignment of collector/desorb subassembly 24.

The construction of collector/desorb subassembly 24 is shown in greater detail in FIGS. 2 and 3. A series of circumferentially spaced nonconductive radial vanes 48 connected to outer hub 32 support an inner hub 50. Radial vanes 48 also support a metal ribbon 52 (e.g., molybdenum coated with an organic polymer such as polymerized silicone), which terminates at either end at outer hub 32 and inner hub 50, and is spiral-wound about inner hub 50.

Further details of metal ribbon 52 are apparent from FIG. 3. Metal ribbon 52 is longitudinally split along nearly its entire length, and thus comprises a pair of narrow metal strips 54, 56 joined at one end by a metal connecting region 58. When metal ribbon 52 is wound into a spiral, metal connecting region 58 is located at inner hub 50, and the free ends of narrow metal strips 54, 56 are located at outer hub 32.

The free end of one of the narrow metal strips 54 electrically connects to a pair of electrical pins ***60a*, *60b* in outer hub 32, and the free end of the other narrow strip 56 similarly connects to a pair of electrical pins *62a*, *62b* in outer hub 32. Thus, because metal ribbon 52 is split, both pair of electrical pins can easily and conveniently be located on outer hub 32. When collector/desorb subassembly 24 is installed against the proximal end 18 of snout 14, mating electrical connectors (not shown) in insulating sleeve 13** electrically interconnect with each of pins 60a, 60b, 62a, 62b. Through these connectors in insulating sleeve 13, a power section of a power supply (not shown) connects across electrical pins 60a and 62a for electrical resistance heating of metal ribbon 52 to desorb vapors from the residue of materials, such as contraband compound, deposited on ribbon 52. A temperature-measuring section of the power supply connects across electrical pins 60b and 62b to monitor the resistance of metal ribbon 52 to determine its temperature. A feedback circuit in the power supply controls the temperature to a desired set point.

It will be appreciated that splitting metal ribbon 52 increases the length of the current path separating electrical pins 60a and 62a, and decreases its width. This increases the resistance across metal ribbon 52 (i.e., electrical pins 60a and 62a) without substantially changing its surface area. Increasing resistance in this manner decreases the amount of current that must be employed to supply a given amount of power to metal ribbon 52.

Figure 4:
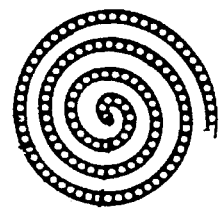
FIG. 4 is an end view of an alternative desorb site subassembly utilizing a metal bundle of coated tubes in contact with a spiral-wound metal foil as a substrate.
Figure 5:
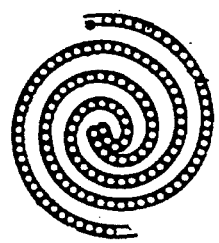
FIG. 5 is an end view of an alternative desorb site subassembly utilizing a metal bundle of coated tubes in contact with a double spiral-wound metal foil as a substrate.
Figure 6:
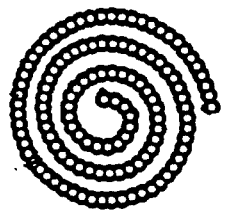
FIG. 6 is an end view of an alternative desorb site subassembly utilizing a metal bundle of coated tubes in contact with a corrugated spiral-wound metal foil as a substrate.
Figure 3:
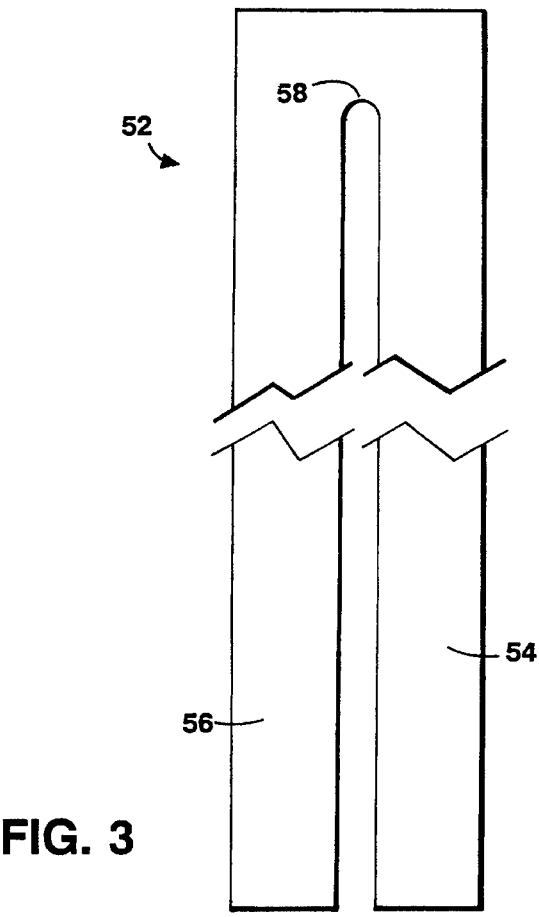
FIG. 3 is a top view of the metal ribbon of FIG. 2 prior to being spiral-wound.

Alternate collector/desorb subassemblies are shown in FIGS. 4–6, and are described in greater detail in aforementioned U.S. Pat. No. 5,092,217.

Operation

Figure 7A:
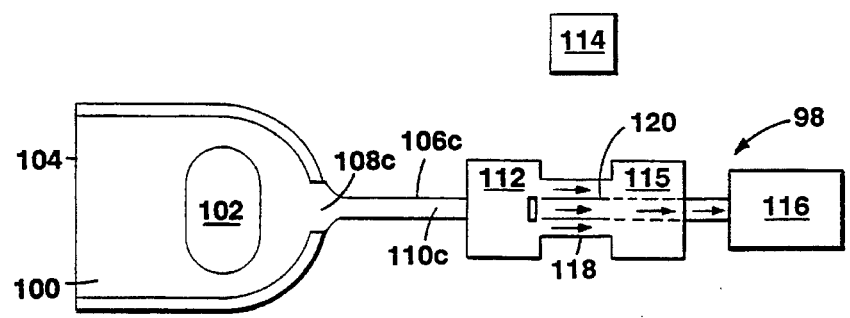
FIG. 7A and FIG. 7B are schematic top and side view diagrams, respectively, showing a portal detector.
Figure 7B:
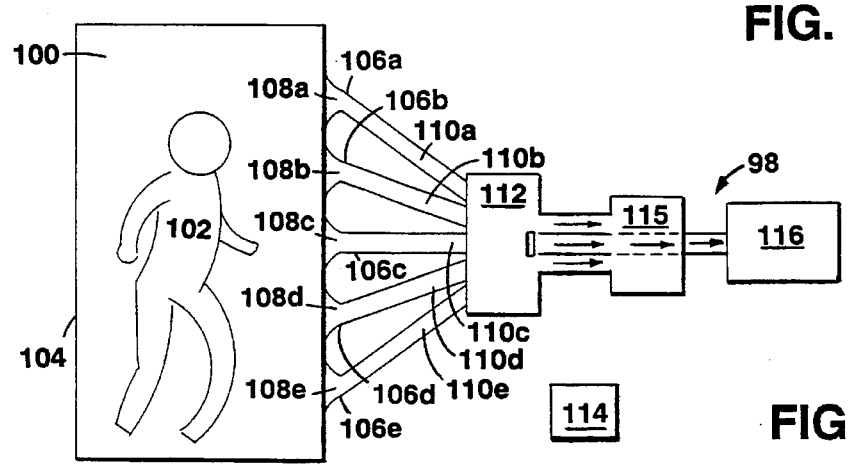

FIGS. 7A and 7B show the configuration of a typical portal-type vapor detector 98. The portal 100, a box into which the subject or object to be sampled 102 (e.g. a person, a piece of luggage, etc.) enters or is placed, is approximately 0.75 meters wide, 1.25 meters deep, and 2.5 meters high. One side 104 of portal 100 is open to atmosphere. Five intake ports 106a–e vertically line the wall opposite this open side. Each intake port 106a–e consists of a rectangular funnel 108a–e, 40 cm high by 25 cm wide, connected to a pipe 110a–e 8 cm in diameter. The centers of the five funnels 108a–e are located 20, 60, 100, 140, and 180 cm from the floor, respectively. The five pipes 110a–e connect to a mixing chamber 112 that houses a collector 113.

Collector 113 is similar in configuration to that of the various embodiments of collector/desorb subassembly 24 shown in FIGS. 2–5. After a sampling cycle completes, collector 113 is mechanically moved (e.g., manually or by a rotating arm, carousel, etc.) to a vapor/particle sensor 114, which may include a high-speed gas chromatograph, a pyrolyzer, and a nitric oxide detector, as described in greater detail in aforementioned U.S. Pat. No. 5,092,217.

The sampling cycle initiates when an object or person enters or is placed in portal 100, triggering a pressure switch (not shown) located in the floor of portal 100. Alternatively, the cycle can be initiated manually, by the operator actuating a separate switch (not shown). During sampling, two computer-controlled blowers 115, 116, coupled respectively to mixing box 112 by concentric pipes 118, 120, operate for a predetermined length of time, sucking ambient room air through the open side 104 of the portal 100 at a known flow rate. This sample air passes around the subject 102 and into the five funnels 108a–e, where it then flows into the mixing chamber 112. Collector 113 is located at the inlet of pipe 120. Thus, controlling the relative flow rates of blowers 115, 116 determines the fraction of the sample air that passes through collector 113. Collector 112 then traps the vapors and particles present in this fraction of the sample air for later desorption and analysis by vapor/particle sensor 114.

Calibrating the portal vapor detector shown in FIGS. 7A and 7B using the pulsed contraband vapor generator 10 of FIG. 1 requires the use of a contraband solution of known concentration. To prepare this solution, known quantities of a particular contraband (e.g., explosives, narcotics, perfume, etc.) are dissolved into a known volume of solvent. The concentration and solvent type vary with the application. For example, calibration solutions for use in explosives detectors are typically acetone-based, and have an explosives concentration on the order of micromoles. These calibration solutions may be prepared in advance and delivered to field operators in sealed vials.

The calibration procedure consists of loosening clamp 40 to remove both back plate 42 and collector/desorb subassembly 24. At this time, metal ribbon 52 in collector/desorb subassembly 24 is at room temperature, and snout 14 is at the preset temperature maintained by the thermostatic controller for heater rods 25. Using a syringe, a known of amount of calibration solution, typically 1–10 microliters, is injected onto the metal ribbon 52. The assembly is then reinstalled into the pulsed vapor generator 10, and clamp 40 closed. Pulsed vapor generator 10 is then positioned in the desired region of the portal 100. For example, if the sensitivity of the upper region of portal 50 were to be determined, snout 14 could be inserted into rectangular funnel 108a.

When vapor generator 10 is positioned as desired, an electronic controller (not shown) simultaneously begins the sampling mode of the portal detector 98, and energizes the power supply connected across electrical pins 60a and 62a, thereby resistance-heating metal ribbon 52. As metallic ribbon coil 52 heats, the vapors from explosive particles contained in the solution deposited on its surface desorb into the surrounding air.

The controller also activates the valved source of pressurized air connected to the inlet of tube 38, supplying filtered air to tube 38 at a flow rate that is very low with respect to the flow rate of blower 115. Air entering the interior region of collector/desorb subassembly 24 through air passage 36 is guided, by back plate 42, axially over the surface of metal ribbon 52. After passing over ribbon 52, the "desorb air," which contains explosive vapors, then passes through the frusto-conical funnel portion 22 of air passage 20. Because the surface of this passage is heated, desorbed explosives vapors entrained in the desorb air do not condense on the surface before exiting at the distal end of snout 14.

The desorb air then flows through, e.g., pipe 110a and mixer box 112 to collector 113. Collector 113 traps a fraction of the explosive vapors, as determined by the relative volume flow rates of blowers 115, 116. After the termination of a normal sampling cycle, collector 113 is mechanically moved to vapor/particle sensor 114, where collected vapors and/or particles are analyzed.

Because a known amount of explosives is injected onto, and desorbed from, the metal ribbon 52 of the vapor generator 10, and since the flow rate of the blower is both known and very high with respect to the flow rate of air introduced into pulse vapor generator 10 through tube 38, collector 113 is exposed to a known mass of explosives in a known volume of air. Thus, vapor generator 10 allows the performance and sensitivity of collector 113 and vapor/particle sensor 114 to be assessed quantitatively as well as qualitatively.

Other embodiments are within the claims.

What is claimed is:

1. Apparatus for calibrating a detector of contraband compound vapor or particles, comprising:

a desorb site for receiving a known amount of a solution having a known concentration of said contraband compound;

a heating element of a first heater for heating said desorb site to produce contraband compound vapors;

a sealed and resealable chamber for enclosing said desorb site;

a snout defining a fluid flow passage in communication with said chamber;

a second heater adapted to heat said snout; and a gas supply line in communication with said chamber, said gas supply line supplying gas to said chamber to entrain at least a portion of said contraband compound vapors in a gas stream exiting said chamber through said fluid flow passage.

2. The apparatus of claim 1 wherein said desorb site is generally of the same design as a collector employed in said detector of contraband compound vapor.

3. The apparatus of claim 2 wherein said desorb site comprises a metal ribbon wound about an inner hub.

4. The apparatus of claim 3 wherein said heating element comprises said metal ribbon.

5. The apparatus of claim 3 wherein said metal ribbon is longitudinally split along at least a portion of its length.

6. The apparatus of claim 3 wherein said gas supply line is in communication with said chamber to deliver gas to said metal ribbon.

7. The apparatus of claim 1 wherein said snout is sized to be inserted into an inlet funnel in a portal-type detector of contraband compound vapor.

8. The apparatus of claim 1 wherein said gas supply line supplies air to said chamber.

9. A method for calibrating a detector of contraband compound vapor or particles, comprising:

preparing a solution having a known concentration of said contraband compound;

applying a known amount of said solution to a desorb site;

sealing said desorb site in a chamber;

heating said desorb site to produce contraband compound vapors;

supplying gas to said chamber to entrain at least a portion of said contraband compound vapors in a gas stream; and delivering said gas stream containing contraband compound vapors to said detector of contraband compound vapor.

10. The method of claim 9 wherein said desorb site is generally of the same design as a collector employed in said detector of contraband compound vapor.

11. The method of claim 10 wherein said desorb site comprises a metal ribbon wound about an inner hub.

12. The method of claim 11 wherein said heating comprises electrical resistance heating of said metal ribbon.

13. The apparatus of claim 11 wherein said metal ribbon is longitudinally split along at least a portion of its length.

14. The method of claim 11 wherein supplying gas to said chamber causes gas to flow across the surface of said metal ribbon.

15. The method of claim 9 wherein air is supplied to said chamber to entrain at least a portion of said contraband compound vapors in an air stream.

16. A method for calibrating a detector of contraband compound vapor or particles, comprising:

preparing a solution having a known concentration of said contraband compound;

applying a known amount of said solution to a desorb site;

sealing said desorb site in a chamber;

heating said desorb site to produce contraband compound vapors;

supplying gas to said chamber to entrain at least a portion of said contraband compound vapors in a gas stream;

delivering said gas stream containing contraband compound vapors to said detector of contraband compound vapor through an interior passage of a hollow snout attached to said chamber, and heating said snout to prevent condensation of said contraband compound vapor on a surface of said interior passage.

17. The method of claim 16 and further comprising the step of inserting said snout into an inlet funnel in a portal-type detector of contraband compound vapor.

\* \* \* \* \*

UNITED STATES PATENT AND TRADEMARK OFFICE
CERTIFICATE OF CORRECTION

PATENT NO. : 5,493,890
DATED : February 27, 1996

Page 1 of 2

INVENTOR(S) : Daniel A. Dussault, William A. Curby, Stephen J. MacDonald, Edward E. A. Bromberg It is certified that error appears in the above-indentified patent and that said Letters Patent is hereby corrected as shown below:

On the title page: Item [56] Reference Cited:

Please add the following after column 2 of the first page of the patent, after "5,092,155   3/1992   Rounbehler et al. . . . . . 73/23.41":

```
--  5,092,217   3/1992     Achter et al.  . . . 86/1.1
    4,534,204   8/1985     Bergquist  . . . . . 73/1 G
    4,531,398   7/1985     Di Benedetto et al. 73/1 G
    4,467,038   8/1984     Scott  . . . . . . . . . . .
    4,305,724   12/1981    Micko  . . . . . . . . . . .
    4,220,452   9/1980     Bray . . . . . . . . . . . .
    4,053,281   10/1977    Carter . . . . . . . . . . .
```

UNITED STATES PATENT AND TRADEMARK OFFICE
CERTIFICATE OF CORRECTION

PATENT NO. : 5,493,890
DATED : February 27, 1996
INVENTOR(S) : Daniel A. Dussault, William A. Curby, Stephen J. MacDonald, Edward E.A. Bromberg It is certified that error appears in the above-indentified patent and that said Letters Patent is hereby corrected as shown below:

Cont.

OTHER PUBLICATIONS

Bromberg et al., "Vapor Generation for Use in Explosive Portal Detection Devices," Advances in Analysis and Detection of Explosives, March 1993, 473-484

Fraim et al., "Efficient Collection of Explosive Vapors, Particles and Aerosols," Proceedings of the First International Symposium on Explosive Detection Technology, February 1992, 559-565

MacDonald et al., "Calibration Methods for Explosives Detectors," Proceedings of the First International Symposium on Explosive Detection Technology, February 1992, 584-588

Rounbehler et al., "Analysis of Explosives Using High Speed Gas Chromatography with Chemiluminescent Detection," Proceedings of the First International Symposium on Explosive Detection Technology, February 1992, 703-713 --

Signed and Sealed this

Eighteenth Day of August, 1998

Attest:

BRUCE LEHMAN

Attesting Officer

Commissioner of Patents and Trademarks